United States Patent
Lee et al.

(10) Patent No.: US 9,156,974 B2
(45) Date of Patent: Oct. 13, 2015

(54) METHOD OF PREPARING A SUPER ABSORBENT POLYMER AND A SUPER ABSORBENT POLYMER PREPARED THEREFROM

(71) Applicant: LG CHEM, LTD., Seoul (KR)

(72) Inventors: Yong Hun Lee, Daejeon (KR); Kyu Pal Kim, Daejeon (KR); Chang Sun Han, Daejeon (KR); Gi Cheul Kim, Daejeon (KR); Chul Hee Ryu, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/359,876

(22) PCT Filed: Nov. 15, 2013

(86) PCT No.: PCT/KR2013/010380
§ 371 (c)(1),
(2) Date: May 21, 2014

(87) PCT Pub. No.: WO2014/077612
PCT Pub. Date: May 22, 2014

(65) Prior Publication Data
US 2015/0259522 A1    Sep. 17, 2015

(30) Foreign Application Priority Data

Nov. 15, 2012 (KR) .................. 10-2012-0129559
Nov. 14, 2013 (KR) .................. 10-2013-0138510

(51) Int. Cl.
*C08F 20/06* (2006.01)
*C08J 3/05* (2006.01)
*C08J 11/04* (2006.01)
*C08L 33/08* (2006.01)

(52) U.S. Cl.
CPC ........... *C08L 33/08* (2013.01); *C08L 2205/025* (2013.01)

(58) Field of Classification Search
CPC ........... C08F 20/06; C08J 3/005; C08J 3/075; C08J 11/04; C08J 11/06; B01J 20/261; B01J 20/267
USPC ........................................... 525/221; 502/402
See application file for complete search history.

(56) References Cited

U.S. PATENT DOCUMENTS

| 5,122,544 A | 6/1992 | Bailey et al. |
| 5,478,879 A | 12/1995 | Kajikawa et al. |
| 2009/0305884 A1* | 12/2009 | Sakamoto et al. ............ 502/402 |
| 2010/0234531 A1 | 9/2010 | Frank |

FOREIGN PATENT DOCUMENTS

| CN | 1636629 A | 7/2005 |
| CN | 1847289 A | 10/2006 |
| KR | 10-2012-0047035 A | 5/2012 |
| KR | 10-2012-0054836 A | 5/2012 |
| KR | 10-2012-0059169 A | 6/2012 |
| WO | 2006/101271 A1 | 9/2006 |
| WO | 2008/038840 A1 | 4/2008 |

* cited by examiner

*Primary Examiner* — Vu A Nguyen
(74) *Attorney, Agent, or Firm* — Dentons US LLP

(57) ABSTRACT

A method of preparing a super absorbent polymer (SAP) includes the steps of preparing a first hydrogel polymer by carrying out a thermal polymerization or photo polymerization of a monomer composition including a water-soluble ethylene-based unsaturated monomer and a polymerization initiator; preparing a second hydrogel polymer by carrying out a thermal polymerization or photo polymerization of a monomer composition including a water-soluble ethylene-based unsaturated monomer and a polymerization initiator; drying and milling the first hydrogel polymer and distributing the first hydrogel polymer into a fine powder having a particle diameter below 150 μm and a base resin having a particle diameter of 150 μm to 850 μm; fabricating a reassembled body of the fine powder by mixing the fine powder and the second hydrogel polymer; and mixing the reassembled body of the fine powder with the first hydrogel polymer, and drying and milling the same.

12 Claims, No Drawings

METHOD OF PREPARING A SUPER ABSORBENT POLYMER AND A SUPER ABSORBENT POLYMER PREPARED THEREFROM

This application is a 35 USC §371 National Stage entry of International Application No. PCT/KR2012/010380, filed on Nov. 15, 2013, and claims priority to Korean Application Nos. 10-2012-0129559, filed on Nov. 15, 2012, and 10-2013-0138510, filed on Nov. 14, 2013, all of which are hereby incorporated by reference in their entirety.

BACKGROUND OF THE INVENTION (a) Field of the Invention

The present invention relates to a method of preparing a super absorbent polymer and a super absorbent polymer prepared therefrom. Specifically, the present invention relates to a method of preparing a super absorbent polymer having high water holding capacity and fine powder aggregation strength without decrease of absorbing power under pressure and penetrability.

(b) Description of the Related Art

Super absorbent polymer (SAP) is a synthetic polymer material having a function of absorbing water about 5 hundred times to about 1 thousand times of the weight of itself, and it has been differently named as super absorbency material (SAM), absorbent gel material (AGM), and so on by developing enterprises. The SAP disclosed above was started to be commercialized for sanitary items and is now being used widely to a water combination soil for horticulture, a water-stop material for civil engineering and construction, a nursery sheet, a freshness preservative in a food distribution field, a poultice material, and the like in addition to the sanitary fittings like a paper diaper for a child.

An inverse suspension polymerization method or an aqueous polymerization method is known as a method of preparing super absorbent polymer. For example, the inverse suspension polymerization is disclosed in Japanese Patent Publication Nos. Sho56-161408, Sho57-158209, Sho57-198714, and so on. As the aqueous polymerization method, a thermal polymerization method polymerizing a hydrogel polymer while fracturing and cooling the same in a kneader equipped with a plurality of spindles, and a photo-polymerization method that exposes a high-concentrated aqueous solution on a belt to a UV ray and the like so as to carry out the polymerization and the dry at the same time are known.

Generally, the hydrogel polymer obtained by said polymerization reaction comes into the market in the form of powder after it is dried and milled.

At this time, the fine powders (fines) having the particle diameter of about 150 µm or less may be formed during the cutting, crashing, and milling step of the dried polymer. It is considered undesirable to use the SAP particles including the fine powders to hygiene goods such as a baby diapers and an adult urinary incontinence device because it may be moved before being used or may show decreased properties.

Therefore, the process for excluding the fine powders so that the fine powder is not included in the final product or the reassembling process for aggregating the fine powder to be normal particle size is needed. At this time, it is important to have high aggregation strength so that the particles do not crushed again after the reassembling process. The reassembling process is generally carried out in a wet condition for raising the aggregation strength. At this time, the more moisture content of the fine powders, the more aggregation strength but it is not easy to handle the same in the reassembling process, and the less moisture content, the easier reassembling process but the aggregation strength is low and it may be easily crushed again after the reassembling process.

SUMMARY OF THE INVENTION

For resolving the problems of prior technologies, it is an object of the present invention to provide a method of preparing a SAP having high water holding capacity and fine powder aggregation strength without decrease of absorbing power under pressure and penetrability and a SAP prepared therefrom.

To achieve the object, the present invention provides a method of preparing a SAP, including the steps of:

preparing a first hydrogel polymer by carrying out a thermal polymerization or photo polymerization of a monomer composition including a water-soluble ethylene-based unsaturated monomer and a polymerization initiator;

preparing a second hydrogel polymer by carrying out a thermal polymerization or photo polymerization of a monomer composition including a water-soluble ethylene-based unsaturated monomer and a polymerization initiator;

drying and milling the first hydrogel polymer and distributing the first hydrogel polymer into a fine powder having a particle diameter below 150 µm and a base resin having a particle diameter of 150 µm to 850 µm;

fabricating a reassembled body of the fine powder by mixing the fine powder and the second hydrogel polymer; and mixing the reassembled body of the fine powder with the first hydrogel polymer, and drying and milling the reassembled body of the fine powder mixed with the first hydrogel polymer, wherein the second hydrogel polymer has higher water holding capacity than the first hydrogel polymer.

The present invention also provides a SAP prepared by the method.

According to the present invention, it is possible to obtain a super absorbent polymer having high water holding capacity and fine powder aggregation strength without decrease of absorbing power under pressure and penetrability.

DETAILED DESCRIPTION OF THE EMBODIMENTS

The method of preparing a SAP, including the steps of: preparing a first hydrogel polymer by carrying out a thermal polymerization or photo polymerization of a monomer composition including a water-soluble ethylene-based unsaturated monomer and a polymerization initiator; preparing a second hydrogel polymer by carrying out a thermal polymerization or photo polymerization of a monomer composition including a water-soluble ethylene-based unsaturated monomer and a polymerization initiator; drying and milling the first hydrogel polymer and distributing the first hydrogel polymer into a fine powder having a particle diameter below 150 µm and a base resin having a particle diameter of 150 µm to 850 µm; fabricating a reassembled body of the fine powder by mixing the fine powder and the second hydrogel polymer; and mixing the reassembled body of the fine powder with the first hydrogel polymer, and drying and milling the reassembled body of the fine powder mixed with the first hydrogel polymer, wherein the second hydrogel polymer has higher water holding capacity than the first hydrogel polymer.

And, the SAP of the present invention is prepared by said method.

Since the present invention can be variously modified and have various examples, specific embodiments of the present invention are explained in this description. However, it is not intended to limit the present invention to the specific examples and it must be understood that the present invention includes every modifications, equivalents, or replacements included in the idea and technical scope of the present invention.

Hereinafter, the method of preparing the SAP of the present invention and the SAP prepared therefrom are explained in more detail.

According to one embodiment of the present invention, the present invention provides a method of preparing a SAP, including the steps of: preparing a first hydrogel polymer by carrying out a thermal polymerization or photo polymerization of a monomer composition including a water-soluble ethylene-based unsaturated monomer and a polymerization initiator; preparing a second hydrogel polymer by carrying out a thermal polymerization or photo polymerization of a monomer composition including a water-soluble ethylene-based unsaturated monomer and a polymerization initiator; drying and milling the first hydrogel polymer and distributing the first hydrogel polymer into a fine powder having a particle diameter below 150 μm and a base resin having a particle diameter of 150 μm to 850 μm; fabricating a reassembled body of the fine powder by mixing the fine powder and the second hydrogel polymer; and mixing the reassembled body of the fine powder with the first hydrogel polymer, and drying and milling the reassembled body of the fine powder mixed with the first hydrogel polymer, wherein the second hydrogel polymer has higher water holding capacity than the first hydrogel polymer.

In the preparation method of the SAP of the present invention, the first hydrogel polymer is prepared by carrying out the thermal polymerization or photo polymerization of the monomer composition including the water-soluble ethylene-based unsaturated monomer and the polymerization initiator.

The monomer composition, the raw material of the SAP, includes the water-soluble ethylene-based unsaturated monomer and the polymerization initiator.

As the water-soluble ethylene-based unsaturated monomer, any monomer that is generally used to the preparation of the SAP may be used unlimitedly. For example, one or more monomers selected from the group consisting of an anionic monomer and a salt thereof, a nonionic hydrophilic monomer, and an unsaturated monomer containing amino group and a quaternary compound thereof may be used.

Concretely, one or more compounds selected from the group consisting of an anionic monomer such as (meth)acrylic acid, maleic anhydride, fumalic acid, crotonic acid, itaconic acid, 2-acryloylethane sulfonic acid, 2-methacryloylethane sulfonic acid, 2-(meth)acryloylpropane sulfonic acid, and 2-(meth)acrylamide-2-methyl propane sulfonic acid, and a salt thereof; a nonionic hydrophilic monomer such as (meth)acrylamide, N-substituted (meth)acrylate, 2-hydroxyethyl(meth)acrylate, 2-hydroxypropyl(meth)acrylate, methoxypolyethyleneglycol(meth)acrylate, and polyethyleneglycol(meth)acrylate; and an unsaturated monomer containing amino group such as (N,N)-dimethylaminoethyl(meth)acrylate and (N,N)-dimethylaminopropyl(meth)acrylate, and a quaternary compound thereof may be used.

More preferably, acrylic acid or a salt thereof, for example acrylic acid or an alkali metal salt thereof like sodium acrylate, may be used. By using such monomer, it becomes possible to prepare the SAP having better properties. In the case of using the alkali metal salt of acrylic acid, it is possible to use acrylic acid after neutralizing the same with a basic compound such as sodium hydroxide (NaOH).

The concentration of the water-soluble ethylene-based unsaturated monomer may be about 20 to about 60 weight %, preferably about 40 to about 50 weight %, in the monomer composition including the raw materials of the SAP and the solvent, and it may be controlled to be an adequate concentration by considering the polymerization time and the reaction conditions. However, when the concentration of the monomer is too low, the yield of the SAP is low and there may be a problem with economics. On the contrary to this, when the concentration is too high, there may be problems on the process that some of the monomer may be extracted or the milling efficiency of the prepared hydrogel polymer appears to be low in the milling process, and thus the properties of the SAP may decrease.

In the preparation method of the SAP of the present invention, the polymerization initiator used in the polymerization is not limited particularly if it is what is generally used to the preparation of the SAP.

Concretely, the polymerization initiator may be a thermal polymerization initiator or a photo polymerization initiator by UV irradiation, according to the polymerization method. However, even in the case of photo polymerization method, a thermal polymerization initiator may be additionally included because a certain amount of heat is generated by the irradiation of UV ray and the like and a certain amount of heat is generated according to the progress of the exothermic polymerization reaction.

Any compound which can form a radical by a light such as an UV ray may be unlimitedly used as the photo polymerization initiator.

The photo polymerization initiator, for example, may be at least one initiator selected from the group consisting of benzoin ether, a dialkyl acetophenone, a hydroxyl alkylketone, phenyl glyoxylate, benzyl dimethyl ketal), an acyl phosphine, and an α-aminoketone. Meanwhile, as the specific example of the acyl phosphine, commercialized lucirin TPO, namely, 2,4,6-trimethyl-benzoyl-trimethyl phosphine oxide may be used. More various photo polymerization initiators are well disclosed in "UV Coatings: Basics, Recent Developments and New Application" written by Reinhold Schwalm, (Elsevier, 2007), p 115, however the example of the photo polymerization initiator is not limited to or by this.

The concentration of the photo polymerization initiator may be about 0.005 to about 1.0 weight % in the monomer composition. When the concentration of the photo polymerization initiator is too low, the polymerization rate may become slow, and when the concentration of the photo polymerization initiator is too high, the molecular weight of the SAP becomes small and the properties may become uneven.

And, as the thermal polymerization initiator, at least one initiator selected from the group consisting of a persulfate-based initiator, an azo-based initiator, hydrogen peroxide, and ascorbic acid may be used. As more specific example of the persulfate-based initiator, there are sodium persulfate ($Na_2S_2O_8$), potassium persulfate ($K_2S_2O_8$), ammonium persulfate (($NH_4)_2S_2O_8$), and the like; and as the example of the azo-based initiator, 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) may be used. More various thermal polymerization initiators are well disclosed in "Principle of Polymerization" written by Odian, (Wiley, 1981), p 203, however the example of the thermal polymerization initiator is not limited to or by this.

The concentration of the thermal polymerization initiator may be about 0.001 to about 0.5 weight % in the monomer composition. When the concentration of the thermal polymerization initiator is too low, the additional thermal polymerization hardly occurs and the effect of adding the thermal polymerization initiator may be poor, and when the concentration of the thermal polymerization initiator is too high, the molecular weight of the SAP becomes small and the properties may become uneven.

According to one embodiment of the present invention, the monomer composition may further include an internal cross-linking agent as the raw material of the SAP. The internal cross-linking agent may be a cross-linking agent having one or more ethylene-based unsaturated functional groups in addition to the functional group which can react with the water-soluble substituents of the water-soluble ethylene-based unsaturated monomer; or a cross-linking agent having two or more functional groups which can react with the water-soluble substituents of the monomer and/or the water-soluble substituents formed by hydrolysis of the monomer.

As the specific example of the internal cross-linking agent, a $C_8$-$C_{12}$ bisacrylamide, bismethacrylamide, a poly(meth)acrylate of $C_2$-$C_{10}$ polyol, or a poly(meth)allylether of $C_2$-$C_{10}$ polyol, and so on may be used, and more specifically, one or more agents selected from the group consisting of N,N'-methylenebis(meth)acrylate, ethyleneoxy(meth)acrylate, polyethyleneoxy(meth)acrylate, propyleneoxy(meth)acrylate, glycerin diacrylate, glycerin triacrylate, trimethylol triacrylate, triallylamine, triarylcyanurate, triallylisocyanate, polyethyleneglycol, diethyleneglycol, and propyleneglycol may be used.

Such internal cross-linking agent may be included in the monomer composition with the concentration of about 0.001 to about 2.0 weight %, and can cross-link the prepared polymer.

In the preparation method of the present invention, the monomer composition of the SAP may further include additives such as a thickener, a plasticizer, a shelf-life stabilizer, an antioxidant, and so on with necessity.

The monomer composition may be prepared in the form of solution that the raw materials such as the water-soluble ethylene-based unsaturated monomer, the photo polymerization initiator, the thermal polymerization initiator, the internal cross-linking agent, and the additives are dissolved in a solvent.

At this time, any solvent which can dissolve said components can be used without limitation, for example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used solely or by combination.

The solvent may be included in the monomer composition in the residual quantity excluding the components disclosed above.

Meanwhile, general method may be used without limitation if the method can prepare a hydrogel polymer from such monomer composition by carrying out the thermal polymerization or photo polymerization.

Specifically, the polymerization method is largely classified into the thermal polymerization and the photo polymerization according to the polymerization energy source, at this time, the thermal polymerization may be carried out in the reactor like kneader equipped with agitating spindles and the photo polymerization may be carried out in the reactor equipped with movable conveyor belt, however the polymerization methods disclosed above are just the examples and the present invention is not limited to or by the polymerization methods disclosed above.

For example, the hydrogel polymer obtained from the thermal polymerization in the reactor like kneader equipped with the agitating spindles disclosed above by providing hot air thereto or heating the reactor may have the size of centimeters or millimeters when it is discharged from the outlet of the reactor, according to the type of the agitating spindles equipped in the reactor. Specifically, the size of the obtained hydrogel polymer can be variously shown according to the concentration of the monomer composition fed thereto, the feeding speed, and the like, and the hydrogel polymer of which the weight average particle diameter is 2 to 50 mm can be obtained generally.

Furthermore, in the case of the photo polymerization carried out with the reactor equipped with the movable conveyor belt disclosed above, the obtained hydrogel polymer may be a sheet type hydrogel polymer having the width same as the belt. At this time, the thickness of the polymer sheet may vary according to the concentration of the monomer composition fed thereto and the feeding speed, and it is preferable to provide the monomer composition so that the sheet type hydrogel polymer having the width of about 0.5 to about 5 cm is obtained. It is not preferable that the monomer composition is fed so that the thickness of the sheet type polymer becomes too thin because the production efficiency is low, and when the thickness of the sheet type polymer is larger than 5 cm, the polymerization reaction may not be occurred evenly throughout the whole thickness due to its excessively thick thickness.

According to one embodiment of the present invention, the moisture content of the first hydrogel polymer obtained by such method may be about 30 to about 60 weight % and preferably about 40 to about 55 weight %. Meanwhile, throughout the present specification, "moisture content" means the content of moisture in the weight of whole hydrogel polymer, and it means the value that the weight of the dried polymer is subtracted from the weight of the hydrogel polymer. Specifically, the moisture content is defined as the value calculated by measuring the weight loss as water is evaporated from the polymer during the dry process by elevating the temperature of the polymer through infrared heating. At this time, the moisture content is measured by carrying out the dry process with the drying condition of elevating the temperature from room temperature to 180° C. and maintaining the temperature at 180° C., wherein the total drying time is set on 20 minutes including 5 minutes of temperature rising step.

Independently, the second hydrogel polymer is prepared by carrying out the thermal polymerization or photo polymerization of the monomer composition including the water-soluble ethylene-based unsaturated monomer and the polymerization initiator.

The details of the water-soluble ethylene-based unsaturated monomer, the polymerization initiator, the solvent, the internal cross-linking agent, and the additives which are the raw materials for the second hydrogel polymer are the same as the preparation method of the first hydrogel polymer disclosed above.

The second hydrogel polymer of the present invention may be prepared by using the raw materials same as or different from those of the first hydrogel polymer.

The second hydrogel polymer of the present invention has higher water holding capacity (CRC) than the first hydrogel polymer when it is measured according to EDANA WSP 241.2 method. For example, the first hydrogel polymer may have the water holding capacity of about 30 g/g or more, preferably about 30 to about 55 g/g, and the second hydrogel polymer may have the water holding capacity of about 35 g/g or more, preferably about 35 to about 60 g/g.

Furthermore, the second polymer of the present invention has higher water-soluble component content than the first polymer when it is measured according to EDANA WSP 270.2 method. For example, the first polymer may have the water-soluble component content of about 5 to about 30 weight % and the second polymer may have the water-soluble component content of about 6 to about 35 weight %. The water-soluble component means the low molecular weight polymer which is soluble in water.

As disclosed above, since the second polymer of the present invention includes higher content of the water-soluble component than the first polymer, the stickiness and the binding function of the second polymer get better and it becomes possible to raise the binding force between the fine powders in the succeeding reassembling step.

The moisture content of the second hydrogel polymer of the present invention may be about 30 to about 60 weight % and preferably about 40 to about 55 weight %.

The characteristics of the second polymer of the present invention such as the water holding capacity, the moisture content, the water-soluble component content, and the like can be achieved by properly regulating the process conditions of the polymerization process of the second polymer. For example, the second polymer having higher water holding capacity than the first polymer can be prepared by decreasing the amount of the cross-linking agent used or increasing the amount of the initiator used.

Subsequently, the obtained first hydrogel polymer is dried.

At this time, a coarse milling step may be further carried out before the drying step for raising the efficiency of the drying step, as occasion demands.

There is no limitation of the milling machine used at this time. For example, any one device selected from the group consisting of a vertical pulverizer, a turbo cutter, a turbo grinder, a rotary cutter mill, a cutter mill, a disc mill, a shred crusher, a crusher, a chopper, and a disc cutter may be used, but it is not limited to or by said examples.

The coarse milling step may be carried out so that the particle diameter of the first polymer is about 2 to about 10 mm.

It is technically not easy to coarse-mill the first hydrogel polymer to be less than 2 mm due to its high moisture content, and the coarse-milled particles may agglomerate when the particle diameter is less than 2 mm. Meanwhile, when the particle diameter is larger than 10 mm, the increasing effect of the efficiency of the succeeding drying step may be insignificant The first polymer obtained after the polymerization that is coarse-milled or not is dried. At this time, the drying temperature may be about 150 to about 250° C. When the drying temperature is lower than 150° C., there is a concern of that the drying time becomes excessively longer or the properties of the super absorbent polymer formed finally are deteriorated, and when the drying temperature is higher than 250° C., only the surface of the polymer is dried, and thus there is a concern of that fine powder may be generated and the properties of the super absorbent polymer formed finally are deteriorated, The drying temperature may preferably be about 150 to about 200° C., and more preferably about 160 to about 180° C.

Meanwhile, the drying time may be about 20 to about 90 minutes by considering the process efficiency but it is not limited to or by this.

Any general drying method that can be used for drying the hydrogel polymer may be used in the drying step without limitation. Specifically, the drying step may be carried out by the method of supplying a hot air, irradiating an infrared ray, irradiating a microwave, or irradiating an ultraviolet ray, and the like. After the drying step disclosed above is carried out, the moisture content of the first hydrogel polymer may be about 0.05 to about 5 weight %.

Subsequently, the dried first polymer obtained through the drying step is milled. It is preferable that the particle diameter of the polymer powder obtained after the milling step is about 150 to about 850 µm. The milling device used for milling the polymer to be the particle diameter may be a pin mill, a hammer mill, a screw mill, a roll mill, a disc mill, a jog mill, and the like, particularly, but the present invention is not limited to or by above examples.

In the milling step, the fine powder having the diameter less than about 150 µm may be formed. The fine powder below a certain particle size, for example below about 150 µm, is generally called as the ultra-absorbent polymer fine powder, the SAP fine powder, or the fines. The fine powder may be formed not only in the milling step but also a transfer step. If the fine powder is included in a product, handling is difficult and it may cause a gel blocking phenomenon and deteriorate the properties. Therefore, it is preferable to exclude the fine powder or reuse the fine powder to be a normal particle so that the final resin product does not include the same.

Therefore, the milled first polymer is distributed into the fine powder having the particle diameter below 150 µm and the base resin having the particle diameter of 150 µm to 850 µm.

For example of reusing the fine powder, the reassembling process may be carried out for aggregating the fine powders to be a normal particle size of about 150 µm to about 850 µm. The reassembling process is generally carried out at a humidified high temperature condition or while spraying steam for raising the aggregation strength. At this time, the more moisture content, the more aggregation strength but handling is not easy in the reassembling process, and the less moisture content, the easier reassembling process but the aggregation strength is low and it may be easily crushed again after the reassembling process.

According to the preparation method of the present invention, the reassembling step is carried out by mixing the fine powders having the diameter below 150 µm with the second hydrogel polymer. At this time, the second hydrogel polymer may be in a free-swollen state with water. In the present invention, the "free-swollen state with water" means the state that the second polymer absorbs water and is swelled without limit load.

Water may be added to the prepared second hydrogel polymer for free-swelling the second polymer with water. Or, after drying the second hydrogel polymer prepared from the polymerization process, the dried second polymer may be free-swollen by providing water. Furthermore, after drying the second polymer and before swelling the same with water, a crashing step for making the second polymer of proper particle size or a distributing step may be carried out in addition.

The second polymer free-swollen with water may contain about 50 to about 50,000 weight %, preferably about 50 to about 200 weight %, of water, based on the total weight of the second polymer.

Since the second hydrogel polymer has high moisture content, it may play roles of a water transfer medium for providing moisture to the fine powders and a binder for aggregating the fine powders at the same time. Therefore, it is possible to aggregate the fine powders more uniformly and fabricate the reassembled polymer having high aggregation strength rather than only water was provided to the fine powders.

According to one embodiment of the present invention, the second hydrogel polymer may be a state before milling after the polymerization step or a state after the polymerization, drying, and milling processes unlimitedly, if the second hydrogel polymer is a moisturized state or a free-swollen state with water.

And, as disclosed above, since the second hydrogel polymer of the present invention is prepared so as to have higher water holding capacity than the first polymer, the reassembled polymer formed by aggregating the same with the fine powders can also have high water holding capacity.

According to one embodiment of the present invention, it is possible to reassemble the powder by mixing about 10 to about 200 parts by weight of the second hydrogel polymer with 100 parts by weight of the fine powder, and preferably by mixing about 20 to about 150 parts by weight of the second hydrogel polymer with 100 parts by weight of the fine powder. When the second hydrogel polymer that is free-swollen with water is mixed with the fine particles in a proper ratio, it is possible to exhibit the enhancing effect of the aggregation strength due to said mixing.

Through the reassembling process, the fine powders are aggregated and the reassembled body of the fine powder is formed. the reassembled body of the fine powder may have the particle diameter over about 150 μm and not exceeding 50 mm, and preferably the particle diameter of about 300 μm to about 30 mm. Furthermore, the phenomenon that the reassembled body is crashed into the fine powders is less even in the succeeding drying, milling, and surface treating steps, because the reassembled body of the fine powder of the present invention has high aggregation strength.

The reassembled body of the fine powder is mixed with the first hydrogel polymer. The first hydrogel polymer is the hydrogel polymer prepared by the polymerization of the monomer composition before the drying step in the preparation step of the first polymer disclosed above. And, it may be mixed with the first polymer that is coarse-milled after the polymerization step.

After the step of mixing the reassembled body of the fine powder and the first hydrogel polymer, the final SAP can be obtained by further carrying out the step of drying and milling the mixed polymer, that is, the polymer which the reassembled body of the fine powder mixed with the first hydrogel polymer. At this time, the effectiveness of the process can be achieved by introducing the polymer mixture in which the reassembled body of the fine powder and the first hydrogel polymer are mixed into the process of preparing the final SAP from the original first polymer and drying and milling the same.

At this time, the drying temperature and the drying time of the drying step are the same as the drying method of the first hydrogel polymer disclosed above.

After carrying out the drying process, the moisture content of the polymer mixture may be about 0.05 to about 5 weight %.

The method may further include the surface cross-linking step of the polymer mixture. And, the method may further include the step of milling or distributing the polymer mixture between the drying step and the surface cross-linking step of the polymer mixture so that the polymer mixture has a particle size suitable to be commercialized The surface cross-linking step is for increasing the cross-linking density near the surface of the SAP particles, regarding the cross-linking density inside the particles. Generally, the surface cross-linking agent is coated on the surface of the SAP particles. Therefore, the reaction occurs on the surface of the SAP particle, and it does not substantially influence on the inside of the particles and improves the cross-linking property of the surface of the particles. Therefore, the surface cross-linked SAP particles have higher degree of cross-linking near the surface than the inside.

At this time, the surface cross-linking agent is not limited particularly if it is a compound which can react to the functional group of the polymer.

In order to improve the characteristics of the SAP, one or more surface cross-linking agents selected from the group consisting of a polyhydric alcohol compound; an epoxy compound; a polyamine compound; a haloepoxy compound; a condensation product of the haloepoxy compound; an oxazoline compound; a mono-, di-, or polyoxazolidinone compound; a cyclic urea compound; a polyvalent metal salt; and an alkylene carbonate compound may be used.

Specifically, as the example of the polyhydric alcohol compound, one or more compounds selected from the group consisting of a mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol may be used.

And, as the example of the epoxy compound, ethylene glycol diglycidyl ether and glycidol may be used, and as the polyamine compound, one or more compounds selected from the group consisting of ethylene diamine, diethylene triamine, triethylene triamine, tetraethylene pentamine, pentaethylene hexamine, polyethylene amine, and polyamide polyamine may be used.

And, epichlorohydrin, epibromohydrin, and α-methylephichlorohydrin may be used as the haloepoxy compound. 2-oxazolidinone, for example, may be used as the mono-, di- or polyoxazolidinone compound.

And, ethylene carbonate may be used as the alkylene carbonate compound. These compounds may be used solely or by combination. Meanwhile, in order to raising the efficiency of the surface cross-linking reaction process, it is preferable to use one or more polyhydric alcohol compounds among said surface cross-linking agent, and it is more preferable to use a $C_2$-$C_{10}$ polyhydric alcohol compound.

The amount of the surface cross-linking agent added may be suitably regulated according to the kind of surface cross-linking agent or the reaction conditions, and normally the amount may be about 0.001 to about 5 parts by weight, preferably about 0.01 to about 3 parts by weight, and more preferably about 0.05 to about 2 parts by weight per 100 parts by weight of the polymer.

When the amount of the surface cross-linking agent used is too small, the surface cross-linking reaction may not be occurred practically, and when the amount is larger than 5 parts by weight per 100 parts by weight of the polymer, the water holding capacity and the properties may be decreased due to excessive surface cross-linking reaction.

The surface cross-linking reaction and drying may be carried out at the same time by heating the polymer particles to which the surface cross-linking agent is added.

The means for elevating temperature for the surface cross-linking reaction is not limited particularly. For example, a heating medium may be provided or a heat source may be directly provided for elevating temperature. At this time, a hot fluid such as steam, hot air, hot oil, and the like may be used as the usable heating medium but the present invention is not limited to or by them. And the temperature of the heating medium may be properly selected by considering the means of the heating medium, the temperature rising speed, and the target temperature. Meanwhile, as the heat source provided directly, an electric heating or a gas heating may be used but the present invention is not limited to or by them.

The SAP having high water holding capacity and fine powder aggregation strength can be obtained according to the preparation method of the present invention. For example, the SAP prepared according to the preparation method of the present invention may have the water holding capacity of about 20 to about 50 g/g, and preferably about 25 to about 45 g/g, and may have the fine powder content of about 5 weight % or less, preferably about 4 weight % or less, and more preferably about 3 weight % or less.

According to another embodiment of the present invention, the SAP prepared by the preparation method is provided.

More concretely, in the SAP of the present invention, the content of the fine powder of which the particle diameter is below 150 μm is about 5 weight % or less, preferably about 4 weight % or less, and more preferably about 3 weight % or less.

Furthermore, the SAP of the present invention may show high penetrability of about 200 seconds or less, for example, about 50 to about 200 seconds, preferably about 60 to about 200 seconds, and more preferably about 60 to about 180 seconds, when it is measured under the load of 0.3 psi by using a 0.9% salt water solution. And, the SAP may have the water holding capacity of about 20 to about 50 g/g, and preferably about 25 to about 45 g/g, when it is measured according to EDANA WSP 241.2 method.

The SAP of the present invention may be prepared by the method of preparing the SAP disclosed above.

Hereinafter, the present invention is explained in more detail through the following examples. However, the following examples are only for illustrating the present invention, and the scope of the present invention is not limited to or by them.

EXAMPLES

Methods for Measuring the Properties of the Super Absorbent Polymer

Strength of the Reassembled Body of the Fine Powder

The strength of the reassembled body of the fine powder was measured through a ball-mill test by measuring the content of the fine powders which were regenerated from the reassembled body of the fine powder. The ball-mill test was carried out according to the method of measuring the content of the fine powders having the diameter less than 150 μm after putting 20 g of the sample and 10 glass beads having the diameter of 15 mm in a 200 ml container and milling the sample with the rotating speed of 150 rpm for 30 minutes. The less content of the fine powders which were regenerated after the ball-mill test may denote the higher aggregation strength.

Water Holding Capacity

The water holding capacity was measured according to EDANA WSP 241.2 method. After inserting 0.2 g of the sample in a tea bag and soaking the same in 0.9% salt water solution for 30 minutes, the water holding capacity was measured by the method of eliminating water from the sample for 3 minutes with a centrifugal separator set-up to 250G and weighing the sample so as to determine the amount of salt water solution held in the super absorbent polymer.

Absorbing Power Under Pressure

The absorbing power under pressure was measured according to EDANA WSP 242.2 method. After distributing 0.9 g of the sample uniformly in a measuring cylinder and pressing the sample with the pressure of 49.2 g/cm$^2$ (0.7 psi) by using a piston and a weight, the sample was transferred to a schale in which 0.9% salt water solution was contained and absorbed the solution for 60 minutes. The absorbing power under pressure was calculated by dividing the increased weight after 60 minutes by the weight of the sample.

Penetrability

The penetrability was measured by using 0.9% salt water solution under the load of 0.3 psi according to the method disclosed in the literature (Buchholz, F. L. and Graham, A. T., "Modern Superabsorbent Polymer Technology," John Wiley & Sons (1998), page 161).

After putting 0.2 g of the sample in a prepared cylinder, 50 g of 0.9% salt water solution was added thereto and left as it was for 30 minutes. And then, the weight of 0.3 psi was put on the sample to which 0.9% salt water solution was absorbed and left as it was for 1 minute. And then, the time that 0.9% salt water solution passed from the upper limit line to the lower limit line marked beforehand on the cylinder was measured after opening the stopcock at the bottom of the cylinder. Every measurement was carried out at the temperature of 24±1° C. and the relative humidity of 50±10%.

The passage time from the upper limit line to the lower limit line was measured to every sample and the passage time without the SAP was measured.

Penetrability (sec)=Time (sample)−Time (without SAP)  [Equation 1]

Preparation of Super Absorbent Polymer

Preparation Example 1

After putting 500 g of acrylic acid and 2.5 g of ethoxylated (15) trimethylolpropane triacrylate in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was put in a twin-arm kneader of 5 L capacity having spindles of sigma-form, and oxygen dissolved in the aqueous solution was eliminated by feeding nitrogen at 75° C. While stirring the solution, 40 g of 0.3% aqueous solution of L-ascorbic acid and 40 g of the aqueous solution that 0.25 g of potassium persulfate and 3.0 g of hydrogen peroxide were dissolved in 100 g of water were added thereto.

The gel-type resin was formed as the polymerization progressed, and the microgel-type hydrogel polymer was prepared by stirring the same for 30 minutes and separating the gel-type resin. The moisture content of the obtained hydrogel polymer was 40.5%.

The hydrogel polymer was spread on a stainless wire gauze having the hole size of 600 μm to be the thickness of about 30 mm, and dried in a hot air oven at 170° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 40.5 g/g, and the content of the water-soluble component was 11.4%.

Preparation Example 2

After putting 500 g of acrylic acid and 0.5 g of 1,6-hexandiol diacrylate (HDDA) in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was put in a twin-arm kneader of 5 L capacity having spindles of sigma-form, and oxygen dissolved in the aqueous solution was eliminated by feeding nitrogen at 85° C. While stirring the solution, 40 g of 0.3% aqueous solution of L-ascorbic acid and 40 g of the aqueous solution that 5.0 g of potassium persulfate and 3.0 g of hydrogen peroxide were dissolved in 100 g of water were added thereto. The gel-type resin was formed as the polymerization progressed, and the microgel-type hydrogel polymer was prepared by stirring the same for 30 minutes and separating the gel-type resin. The moisture content of the obtained hydrogel polymer was 40.1%. The hydrogel polymer was spread on a stainless wire gauze having the hole size of 600 μm to be the thickness of about 30 mm, and dried in a hot air oven at 180° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 50.1 g/g, and the content of the water-soluble component was 21.4%.

Preparation Example 3

After putting 500 g of acrylic acid and 3.75 g of ethoxylated (15) trimethylolpropane triacrylate in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was put in a twin-arm kneader of 5 L capacity having spindles of sigma-form, and oxygen dissolved in the aqueous solution was eliminated by feeding nitrogen at 75° C. While stirring the solution, 20 g of 0.3% aqueous solution of L-ascorbic acid and 30 g of the aqueous solution that 1.25 g of potassium persulfate and 3.0 g of hydrogen peroxide were dissolved in 100 g of water were added thereto.

The gel-type resin was formed as the polymerization progressed, and the microgel-type hydrogel polymer was prepared by stirring the same for 30 minutes and separating the gel-type resin. The moisture content of the obtained hydrogel polymer was 40.2%. The hydrogel polymer was spread on a stainless wire gauze having the hole size of 600 μm to be the thickness of about 30 mm, and dried in a hot air oven at 160° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 36.2 g/g, and the content of the water-soluble component was 7.3%.

Preparation Example 4

After putting 500 g of acrylic acid and 1.5 g of 1,6-hexandiol diacrylate (HDDA) in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was put in a twin-arm kneader of 5 L capacity having spindles of sigma-form, and oxygen dissolved in the aqueous solution was eliminated by feeding nitrogen at 75° C. While stirring the solution, 20 g of 0.3% aqueous solution of L-ascorbic acid and 30 g of the aqueous solution that 5.0 g of potassium persulfate and 3.0 g of hydrogen peroxide were dissolved in 100 g of water were added thereto.

The gel-type resin was formed as the polymerization progressed, and the microgel-type hydrogel polymer was prepared by stirring the same for 30 minutes and separating the gel-type resin. The moisture content of the obtained hydrogel polymer was 40.1%. The hydrogel polymer was spread on a stainless wire gauze having the hole size of 600 μm to be the thickness of about 30 mm, and dried in a hot air oven at 160° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 38.5 g/g, and the content of the water-soluble component was 14.6%.

Preparation Example 5

After putting 500 g of acrylic acid, 2.25 g of ethoxylated (15) trimethylolpropane triacrylate, and 0.165 g of diphenyl (2,4,6-trimethylbenzoyl)-phosphine oxide in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was cooled to 50° C.

After feeding 500 g of the aqueous solution to a stainless steel container of 250 mm width, 250 mm length, and 30 mm height, the UV polymerization was carried out by irradiating an UV ray (dosage: 10 mW/cm$^2$) to the solution for 90 seconds and the hydrogel polymer was obtained. The moisture content measured after crushing the obtained hydrogel polymer into the size of 2 mm*2 mm was 39.5%.

The obtained hydrogel polymer was spread on a stainless wire gauze having the hole size of 600 μm to be the thickness of about 30 mm, and dried in a hot air oven at 160° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 40.2 g/g, and the content of the water-soluble component was 11.8%.

Preparation Example 6

After putting 500 g of acrylic acid, 0.45 g of 1,6-hexandiol diacrylate (HDDA), and 0.04 g of diphenyl(2,4,6-trimethylbenzoyl)-phosphine oxide in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was cooled to 70° C.

After feeding 500 g of the aqueous solution to a stainless steel container of 250 mm width, 250 mm length, and 30 mm height, the UV polymerization was carried out by irradiating an UV ray (dosage: 10 mW/cm$^2$) to the solution for 90 seconds and the hydrogel polymer was obtained. The moisture content measured after crushing the obtained hydrogel polymer into the size of 2 mm*2 mm was 39.7%.

The obtained hydrogel polymer was spread on a stainless wire gauze having the hole size of 600 μm to be the thickness of about 30 mm, and dried in a hot air oven at 180° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 50.9 g/g, and the content of the water-soluble component was 16.8%.

Preparation Example 7

After putting 500 g of acrylic acid, 2.25 g of ethoxylated (15) trimethylolpropane triacrylate, and 0.04 g of diphenyl(2,4,6-trimethylbenzoyl)-phosphine oxide in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was cooled to 70° C.

After feeding 500 g of the aqueous solution to a stainless steel container of 250 mm width, 250 mm length, and 30 mm height, the UV polymerization was carried out by irradiating an UV ray (dosage: 10 mW/cm$^2$) to the solution for 90 seconds and the hydrogel polymer was obtained. The moisture content measured after crushing the obtained hydrogel polymer into the size of 2 mm*2 mm was 40.1%.

The obtained hydrogel polymer was spread on a stainless wire gauze having the hole size of 600 μm to be the thickness of about 30 mm, and dried in a hot air oven at 160° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 37.4 g/g, and the content of the water-soluble component was 7.7%.

Preparation Example 8

After putting 500 g of acrylic acid, 0.675 g of 1,6-hexandiol diacrylate (HDDA), and 0.2 g of diphenyl(2,4,6-trimethylbenzoyl)-phosphine oxide in a 3 L glass container equipped with a stirrer, a nitrogen feeder, and a thermocouple and dissolving the same, the aqueous solution of the water-soluble unsaturated monomer was prepared by adding 896.4 g of 24.5% sodium hydroxide solution thereto while feeding nitrogen continuously. The aqueous solution of the water-soluble unsaturated monomer was cooled to 50° C.

After feeding 500 g of the aqueous solution to a stainless steel container of 250 mm width, 250 mm length, and 30 mm height, the UV polymerization was carried out by irradiating an UV ray (dosage: 10 mW/cm$^2$) to the solution for 90 seconds and the hydrogel polymer was obtained. The moisture content measured after crushing the obtained hydrogel polymer into the size of 2 mm*2 mm was 39.8%.

The obtained hydrogel polymer was spread on a stainless wire gauze having the hole size of 600 μm to be the thickness of about 30 mm, and dried in a hot air oven at 170° C. for 5 hours. The dried polymer was milled by using a milling machine and the base resin having the particle size of 150~850 μm and the fine powder having the particle diameter less than 150 μm were obtained by distributing the milled polymer with a standard sieve according to ASTM. At this time, the amount of the obtained fine powder was 15 weight % of the dried polymer.

The water holding capacity of the obtained base resin was 39.2 g/g, and the content of the water-soluble component was 16.2%.

Example 1 i) Preparation of Reassembled Body of the Fine Powder 1 g of the base resin (the second polymer) prepared by Preparation Example 2 was swollen with 100 g of water. 100 g of the fine powder particles (the first polymer) less than 150 μm obtained in Preparation Example 1 and 100 g of the swollen second polymer were mixed by using a high-speed rotating agitator so as to form the reassembled body of the fine powder.

ii) Preparation of Base Resin Including the Reassembled Body

The hydrogel polymer including the reassembled body of the fine powder was prepared by introducing 200 g of the reassembled body of the fine powder prepared in step i) to the process of stirring the hydrogel with a kneader in Preparation Example 1 and stirring the same with the hydrogel for 1 minute. The hydrogel polymer was spread on a stainless wire gauze having the hole size of 600 μm to be the thickness of about 30 mm, and dried in a hot air oven at 170° C. for 5 hours. The dried polymer was milled by using a milling machine and the polymer powder having the particle size of 150~850 μm was obtained by distributing the milled polymer with a standard sieve according to ASTM.

iii) Surface Cross-Linking Reaction and Preparation of the Final SAP

The mixture solution of 1.0 g of ethylene carbonate, 4.0 g of water, 0.3 g of oxalic acid, and 0.02 g of silica was added to 100 g of the polymer powder obtained in step ii) and uniformly mixed with the same, and the mixture was reacted while being dried in a hot air oven at 160° C. for 60 minutes. The dried powder was distributed with a standard sieve according to ASTM, and the final SAP having the particle size of 150~850 μm was obtained.

Example 2

The SAP was obtained substantially according to the same method as in Example 1, except that the fine powder particles less than 150 μm obtained in Preparation Example 3 was used as the first polymer and the base resin obtained in Preparation Example 4 was used as the second polymer.

Example 3 i) Preparation of Reassembled Body of the Fine Powder 1 g of the base resin (the second polymer) prepared by Preparation Example 6 was swollen with 100 g of water. 100 g of the fine powder particles (the first polymer) less than 150 μm obtained in Preparation Example 5 and 100 g of the swollen second polymer were mixed by using a high-speed rotating agitator so as to form the reassembled body of the fine powder.

ii) Preparation of Base Resin Including the Reassembled Body

The hydrogel polymer including the reassembled body of the fine powder was prepared by introducing 200 g of the reassembled body of the fine powder prepared in step i) to the step of milling the hydrogel polymer after the UV polymerization for obtaining the hydrogel polymer in Preparation Example 5 and stirring the same with the hydrogel for 1 minute. The hydrogel polymer was spread on a stainless wire gauze having the hole size of 600 μm to be the thickness of about 30 mm, and dried in a hot air oven at 170° C. for 5 hours. The dried polymer was milled by using a milling machine and the polymer powder having the particle size of 150~850 μm was obtained by distributing the milled polymer with a standard sieve according to ASTM.

iii) Surface Cross-Linking Reaction and Preparation of the Final SAP

The mixture solution of 1.0 g of ethylene carbonate, 4.0 g of water, 0.3 g of oxalic acid, and 0.02 g of silica was added to 100 g of the polymer powder obtained in step ii) and uniformly mixed with the same, and the mixture was reacted while being dried in a hot air oven at 160° C. for 60 minutes. The dried powder was distributed with a standard sieve according to ASTM, and the final SAP having the particle size of 150~850 μm was obtained.

Example 4

The SAP was obtained substantially according to the same method as in Example 3, except that the fine powder particles less than 150 μm obtained in Preparation Example 7 was used as the first polymer and the base resin obtained in Preparation Example 8 was used as the second polymer.

Example 5

The SAP was obtained substantially according to the same method as in Example 1, except that the fine powder particles less than 150 μm obtained in Preparation Example 1 was used as the first polymer and the base resin obtained in Preparation Example 6 was used as the second polymer.

Example 6

The SAP was obtained substantially according to the same method as in Example 3, except that the fine powder particles less than 150 μm obtained in Preparation Example 5 was used as the first polymer and the base resin obtained in Preparation Example 2 was used as the second polymer.

Example 7

The SAP was obtained substantially according to the same method as in Example 1, except that the fine powder particles less than 150 μm obtained in Preparation Example 3 was used as the first polymer and the base resin obtained in Preparation Example 1 was used as the second polymer.

Example 8

The SAP was obtained substantially according to the same method as in Example 3, except that the fine powder particles less than 150 μm obtained in Preparation Example 7 was used as the first polymer and the base resin obtained in Preparation Example 5 was used as the second polymer.

Example 9

The SAP was obtained substantially according to the same method as in Example 1, except that the fine powder particles less than 150 μm obtained in Preparation Example 4 was used as the first polymer and the base resin obtained in Preparation Example 2 was used as the second polymer.

Example 10

The SAP was obtained substantially according to the same method as in Example 3, except that the fine powder particles less than 150 μm obtained in Preparation Example 8 was used as the first polymer and the base resin obtained in Preparation Example 6 was used as the second polymer.

Comparative Example 1

The SAP was obtained substantially according to the same method as in Example 1, except that the reassembled body of the fine powder was prepared by mixing 100 g of the fine powder particles less than 150 μm obtained in Preparation Example 1 and 100 g of water with a high-speed rotating agitator in the preparation step of the reassembled body of the fine powder.

Comparative Example 2

The SAP was obtained substantially according to the same method as in Example 2, except that the reassembled body of the fine powder was prepared by mixing 100 g of the fine powder particles less than 150 μm obtained in Preparation Example 3 and 100 g of water with a high-speed rotating agitator in the preparation step of the reassembled body of the fine powder.

Comparative Example 3

The SAP was obtained substantially according to the same method as in Example 3, except that the reassembled body of the fine powder was prepared by mixing 100 g of the fine powder particles less than 150 μm obtained in Preparation Example 5 and 100 g of water with a high-speed rotating agitator in the preparation step of the reassembled body of the fine powder.

Comparative Example 4

The SAP was obtained substantially according to the same method as in Example 4, except that the reassembled body of the fine powder was prepared by mixing 100 g of the fine powder particles less than 150 μm obtained in Preparation Example 7 and 100 g of water with a high-speed rotating agitator in the preparation step of the reassembled body of the fine powder.

Comparative Example 5

The SAP was obtained substantially according to the same method as in Example 1, except that the fine powder particles less than 150 μm obtained in Preparation Example 1 was used as the first polymer and the resin powder obtained in Preparation Example 3 was used as the second polymer.

Comparative Example 6

The SAP was obtained substantially according to the same method as in Example 3, except that the fine powder particles less than 150 μm obtained in Preparation Example 5 was used as the first polymer and the resin powder obtained in Preparation Example 7 was used as the second polymer.

The properties of the SAPs of Examples 1 to 10 and Comparative Examples 1 to 6 were measured and the results are listed in the following Table 1.

TABLE 1

| | | | Properties of final SAP | | | |
|---|---|---|---|---|---|---|
| | First Polymer | Second Polymer | Content of fine powder less than 150 μm (weight %) | Water holding capacity (g/g) | Absorbing power under pressure of 0.7 psi (g/g) | Penetrability (seconds) |
| Example 1 | Preparation Example 1 | Preparation Example 2 | 2.1 | 33.7 | 23.7 | 148 |
| Example 2 | Preparation Example 3 | Preparation Example 4 | 2.6 | 30.8 | 24.7 | 129 |
| Example 3 | Preparation Example 5 | Preparation Example 6 | 2.6 | 33.7 | 23.5 | 152 |
| Example 4 | Preparation Example 7 | Preparation Example 8 | 2.6 | 32.4 | 23.5 | 144 |
| Example 5 | Preparation Example 1 | Preparation Example 6 | 2.0 | 33.8 | 23.7 | 147 |
| Example 6 | Preparation Example 5 | Preparation Example 2 | 2.5 | 33.7 | 23.5 | 151 |
| Example 7 | Preparation Example 3 | Preparation Example 1 | 2.6 | 31.0 | 24.4 | 131 |
| Example 8 | Preparation Example 7 | Preparation Example 5 | 2.6 | 32.4 | 23.6 | 144 |
| Example 9 | Preparation Example 4 | Preparation Example 2 | 2.1 | 31.7 | 24.4 | 160 |
| Example 10 | Preparation Example 8 | Preparation Example 6 | 2.1 | 34.4 | 23.3 | 175 |
| Comparative Example 1 | Preparation Example 1 | — | 4.8 | 34.1 | 23.1 | 286 |
| Comparative Example 2 | Preparation Example 3 | — | 4.4 | 31.6 | 23.8 | 265 |
| Comparative Example 3 | Preparation Example 5 | — | 4.7 | 34.4 | 22.7 | 360 |
| Comparative Example 4 | Preparation Example 7 | — | 4.4 | 33.1 | 22.9 | 225 |
| Comparative Example 5 | Preparation Example 1 | Preparation Example 3 | 3.8 | 34.2 | 23.0 | 262 |
| Comparative Example 6 | Preparation Example 5 | Preparation Example 7 | 4.0 | 34.3 | 22.8 | 288 |

*content of fine powder less than 150 μm (%): result of ball-mill test

Referring to Table 1, the SAPs prepared by the method of the present invention are superior in the water holding capacity, the absorbing power under pressure, and the penetrability without reference to the initiation method of the polymerization. But, it is recognizable that the SAPs of Comparative Examples 5 and 6 of which the water holding capacity and the water-soluble component of the second polymer were higher than the first polymer showed higher content of the fine powder and lower penetrability, compared to Examples 1 and 3.

And, as the result of ball-mill test, it is recognizable that the fine powder particles less than 150 µm is apparently less in the SAPs prepared by the Examples of the present invention. The fine powder may be formed by the friction between the SAP particles during the processes of transferring the SAP or preparing a product in which the SAP is included, and the properties of the SAP included in the product may be less than the properties measured just after the SAP was prepared. However, referring to the ball-mill test, it is recognizable that reisolation of the SAP due to the friction during the process of preparing the product rarely occurs in the SAPs prepared by the Examples of the present invention.

Example 11 i) Preparation of Reassembled Body of the Fine Powder 1 g of the base resin (the second polymer) prepared by Preparation Example 2 was swollen with 100 g of water. 100 g of the fine powder particles (the first polymer) less than 150 µm obtained in Preparation Example 1 and 100 g of the swollen second polymer were mixed by using a high-speed rotating agitator so as to form the reassembled body of the fine powder.

ii) Preparation of Base Resin Including the Reassembled Body

After mixing 200 g of the reassembled body of the fine powder prepared in step i) with the hydrogel polymer obtained in the process of preparing the base resin of Preparation Example 1 simply, the mixed polymer was spread on a stainless wire gauze having the hole size of 600 µm to be the thickness of about 30 mm, and dried in a hot air oven at 170° C. for 5 hours. The dried polymer was milled by using a milling machine and the polymer powder having the particle size of 150~850 µm was obtained by distributing the milled polymer with a standard sieve according to ASTM.

iii) Surface Cross-Linking Reaction and Preparation of the Final SAP

The mixture solution of 1.0 g of ethylene carbonate, 4.0 g of water, 0.3 g of oxalic acid, and 0.02 g of silica was added to 100 g of the polymer powder obtained in step ii) and uniformly mixed with the same, and the mixture was reacted while being dried in a hot air oven at 160° C. for 60 minutes. The dried powder was distributed with a standard sieve according to ASTM, and the final SAP having the particle size of 150~850 µm was obtained.

Example 12

The SAP was obtained substantially according to the same method as in Example 11, except that the fine powder particles less than 150 µm obtained in Preparation Example 3 was used as the first polymer and the base resin obtained in Preparation Example 4 was used as the second polymer.

Example 13 i) Preparation of Reassembled Body of the Fine Powder

After swelling 1 g of the base resin (the second polymer) prepared by Preparation Example 6 with 100 g of water, 100 g of the fine powder particles (the first polymer) less than 150 µm obtained in Preparation Example 5 and 100 g of the swollen second polymer were mixed by using a high-speed rotating agitator so as to form the reassembled body of the fine powder.

ii) Preparation of Base Resin Including the Reassembled Body

After mixing 200 g of the reassembled body of the fine powder prepared in step i) with the hydrogel polymer milled into the size of 2 mm*2 mm in Preparation Example 5 simply, the mixed polymer was spread on a stainless wire gauze having the hole size of 600 µm to be the thickness of about 30 mm, and dried in a hot air oven at 170° C. for 5 hours. The dried polymer was milled by using a milling machine and the polymer powder having the particle size of 150~850 µm was obtained by distributing the milled polymer with a standard sieve according to ASTM.

iii) Surface Cross-Linking Reaction and Preparation of the Final SAP

The mixture solution of 1.0 g of ethylene carbonate, 4.0 g of water, 0.3 g of oxalic acid, and 0.02 g of silica was added to 100 g of the polymer powder obtained in step ii) and uniformly mixed with the same, and the mixture was reacted while being dried in a hot air oven at 160° C. for 60 minutes. The dried powder was distributed with a standard sieve according to ASTM, and the final SAP having the particle size of 150~850 µm was obtained.

Example 14

The SAP was obtained substantially according to the same method as in Example 13, except that the fine powder particles less than 150 µm obtained in Preparation Example 7 was used as the first polymer and the base resin obtained in Preparation Example 8 was used as the second polymer.

Comparative Example 7

The SAP was obtained substantially according to the same method as in Example 11, except that the reassembled body of the fine powder was prepared by mixing 100 g of the fine powder particles less than 150 µm obtained in Preparation Example 1 and 100 g of water with a high-speed rotating agitator in the preparation step of the reassembled body of the fine powder.

Comparative Example 8

The SAP was obtained substantially according to the same method as in Example 12, except that the reassembled body of the fine powder was prepared by mixing 100 g of the fine powder particles less than 150 µm obtained in Preparation Example 3 and 100 g of water with a high-speed rotating agitator in the preparation step of the reassembled body of the fine powder.

Comparative Example 9

The SAP was obtained substantially according to the same method as in Example 13, except that the reassembled body of the fine powder was prepared by mixing 100 g of the fine powder particles less than 150 µm obtained in Preparation Example 5 and 100 g of water with a high-speed rotating agitator in the preparation step of the reassembled body of the fine powder.

Comparative Example 10

The SAP was obtained substantially according to the same method as in Example 14, except that the reassembled body of the fine powder was prepared by mixing 100 g of the fine powder particles less than 150 μm obtained in Preparation Example 7 and 100 g of water with a high-speed rotating agitator in the preparation step of the reassembled body of the fine powder.

The properties of the SAPs of Examples 11 to 14 and Comparative Examples 7 to 10 were measured and the results are listed in the following Table 2.

TABLE 2

| | | | Properties of final SAP | | | |
|---|---|---|---|---|---|---|
| | First Polymer | Second Polymer | Content of fine powder (weight %) | Water holding capacity (g/g) | Absorbing power under pressure of 0.7 psi (g/g) | Penetrability (seconds) |
| Example 11 | Preparation Example 1 | Preparation Example 2 | 2.2 | 33.8 | 23.5 | 149 |
| Example 12 | Preparation Example 3 | Preparation Example 4 | 2.5 | 31.0 | 24.6 | 132 |
| Example 13 | Preparation Example 5 | Preparation Example 6 | 2.1 | 33.8 | 23.4 | 152 |
| Example 14 | Preparation Example 7 | Preparation Example 8 | 2.6 | 32.5 | 23.7 | 146 |
| Comparative Example 7 | Preparation Example 1 | — | 4.9 | 34.0 | 23.0 | 292 |
| Comparative Example 8 | Preparation Example 3 | — | 4.6 | 31.8 | 23.9 | 171 |
| Comparative Example 9 | Preparation Example 5 | — | 4.9 | 34.6 | 23.0 | 352 |
| Comparative Example 10 | Preparation Example 7 | — | 4.6 | 33.1 | 22.7 | 228 |

*content of fine powder less than 150 μm (%): result of ball-mill test

Referring to Table 2, it is recognizable that there was no decrease in the water holding capacity and the penetrability, even in the case of forming the SAP by merely mixing the reassembled body of the fine powder and the first hydrogel polymer without mechanical agitation as in Examples 11 to 14.

Example 15 i) Preparation of Reassembled Body of the Fine Powder

After swelling 2 g of the microgel-type hydrogel polymer (the second polymer) obtained in the middle step of Preparation Example 2 with 100 g of water, 100 g of the fine powder particles (the first polymer) less than 150 μm obtained in Preparation Example 1 and 100 g of the swollen second polymer were mixed by using a high-speed rotating agitator so as to form the reassembled body of the fine powder.

ii) Preparation of Base Resin Including the Reassembled Body

After mixing 200 g of the reassembled body of the fine powder prepared in step i) with the microgel-type hydrogel polymer obtained in the process of preparing the base resin of Preparation Example 1 simply, the mixed polymer was spread on a stainless wire gauze having the hole size of 600 μm to be the thickness of about 30 mm, and dried in a hot air oven at 170° C. for 5 hours. The dried polymer was milled by using a milling machine and the polymer powder having the particle size of 150~850 μm was obtained by distributing the milled polymer with a standard sieve according to ASTM.

iii) Surface Cross-Linking Reaction and Preparation of the Final SAP

The mixture solution of 1.0 g of ethylene carbonate, 4.0 g of water, 0.3 g of oxalic acid, and 0.02 g of silica was added to 100 g of the polymer powder obtained in step ii) and uniformly mixed with the same, and the mixture was reacted while being dried in a hot air oven at 160° C. for 60 minutes.

The dried powder was distributed with a standard sieve according to ASTM, and the final SAP having the particle size of 150~850 μm was obtained.

Example 16

The SAP was obtained substantially according to the same method as in Example 15, except that the fine powder particles less than 150 μm obtained in Preparation Example 3 was used as the first polymer and the microgel-type hydrogel polymer obtained in the middle step of Preparation Example 4 was used as the second polymer.

Example 17 i) Preparation of Reassembled Body of the Fine Powder

After swelling 2 g of the microgel-type hydrogel polymer (the second polymer) obtained in the middle step of Preparation Example 6 with 100 g of water, 100 g of the fine powder particles (the first polymer) less than 150 μm obtained in Preparation Example 5 and 100 g of the swollen second polymer were mixed by using a high-speed rotating agitator so as to form the reassembled body of the fine powder.

ii) Preparation of Base Resin Including the Reassembled Body

After mixing 200 g of the reassembled body of the fine powder prepared in step i) with the hydrogel polymer milled into the size of 2 mm*2 mm in Preparation Example 5 simply, the mixed polymer was spread on a stainless wire gauze having the hole size of 600 μm to be the thickness of about 30 mm, and dried in a hot air oven at 170° C. for 5 hours. The dried polymer was milled by using a milling machine and the polymer powder having the particle size of 150~850 μm was obtained by distributing the milled polymer with a standard sieve according to ASTM.

iii) Surface Cross-Linking Reaction and Preparation of the Final SAP

The mixture solution of 1.0 g of ethylene carbonate, 4.0 g of water, 0.3 g of oxalic acid, and 0.02 g of silica was added to 100 g of the polymer powder obtained in step ii) and uniformly mixed with the same, and the mixture was reacted while being dried in a hot air oven at 160° C. for 60 minutes. The dried powder was distributed with a standard sieve according to ASTM, and the final SAP having the particle size of 150~850 μm was obtained.

Example 18

The SAP was obtained substantially according to the same method as in Example 17, except that the fine powder particles less than 150 μm obtained in Preparation Example 7 was used as the first polymer and the microgel-type hydrogel polymer obtained in the middle step of Preparation Example 8 was used as the second polymer.

The properties of the SAPs of Examples 15 to 18 were measured and the results are listed in the following Table 3.

TABLE 3

| | | | Properties of final SAP | | | |
|---|---|---|---|---|---|---|
| | First Polymer | Second Polymer | Content of fine powder (weight %) | Water holding capacity (g/g) | Absorbing power under pressure of 0.7 psi (g/g) | Penetrability (seconds) |
| Example 15 | Preparation Example 1 | Preparation Example 2 | 2.2 | 33.3 | 23.9 | 138 |
| Example 16 | Preparation Example 3 | Preparation Example 4 | 2.4 | 30.5 | 24.8 | 126 |
| Example 17 | Preparation Example 5 | Preparation Example 6 | 2.1 | 33.2 | 23.6 | 144 |
| Example 18 | Preparation Example 7 | Preparation Example 8 | 2.5 | 32.4 | 23.7 | 137 |

*content of fine powder less than 150 μm (%): result of ball-mill test

Referring to Table 3, it is recognizable that the present invention was effective even the hydrogel polymer before drying after the polymerization, which was not powder phase, was used as the second polymer after it was swollen.

Example 19

The final SAP was obtained substantially according to the same method as in Example 1, except that 5 g of the base resin (the second polymer) prepared by Preparation Example 2 was swollen with 100 g of water, and 100 g of the fine powder particles (the first polymer) less than 150 μm obtained in Preparation Example 1 and 100 g of the swollen second polymer were mixed by using a high-speed rotating agitator so as to form the reassembled body of the fine powder.

Example 20

The final SAP was obtained substantially according to the same method as in Example 1, except that 10 g of the base resin (the second polymer) prepared by Preparation Example 2 was swollen with 100 g of water, and 100 g of the fine powder particles (the first polymer) less than 150 μm obtained in Preparation Example 1 and 100 g of the swollen second polymer were mixed by using a high-speed rotating agitator so as to form the reassembled body of the fine powder.

Example 21

The final SAP was obtained substantially according to the same method as in Example 1, except that 20 g of the base resin (the second polymer) prepared by Preparation Example 2 was swollen with 100 g of water, and 100 g of the fine powder particles (the first polymer) less than 150 μm obtained in Preparation Example 1 and 100 g of the swollen second polymer were mixed by using a high-speed rotating agitator so as to form the reassembled body of the fine powder.

Example 22

The final SAP was obtained substantially according to the same method as in Example 2, except that 1 g of the base resin (the second polymer) prepared by Preparation Example 4 was swollen with 50 g of water, and 100 g of the fine powder particles (the first polymer) less than 150 μm obtained in Preparation Example 3 and 100 g of the swollen second polymer were mixed by using a high-speed rotating agitator so as to form the reassembled body of the fine powder.

Example 23

The final SAP was obtained substantially according to the same method as in Example 2, except that 1 g of the base resin (the second polymer) prepared by Preparation Example 4 was swollen with 150 g of water, and 100 g of the fine powder particles (the first polymer) less than 150 μm obtained in Preparation Example 3 and 100 g of the swollen second polymer were mixed by using a high-speed rotating agitator so as to form the reassembled body of the fine powder.

Example 24

The final SAP was obtained substantially according to the same method as in Example 2, except that 1 g of the base resin (the second polymer) prepared by Preparation Example 4 was swollen with 200 g of water, and 100 g of the fine powder particles (the first polymer) less than 150 μm obtained in Preparation Example 3 and 100 g of the swollen second polymer were mixed by using a high-speed rotating agitator so as to form the reassembled body of the fine powder.

Comparative Example 11

The final SAP was obtained substantially according to the same method as in Example 2, except that the reassembled body of the fine powder was prepared by mixing 100 g of the fine powder particles less than 150 μm obtained in Preparation Example 3 and 50 g of water with a high-speed rotating agitator in the preparation step of the reassembled body of the fine powder.

Comparative Example 12

The final SAP was obtained substantially according to the same method as in Example 2, except that the reassembled body of the fine powder was prepared by mixing 100 g of the fine powder particles less than 150 μm obtained in Preparation Example 3 and 150 g of water with a high-speed rotating agitator in the preparation step of the reassembled body of the fine powder.

Comparative Example 13

The final SAP was obtained substantially according to the same method as in Example 2, except that the reassembled body of the fine powder was prepared by mixing 100 g of the fine powder particles less than 150 μm obtained in Preparation Example 3 and 200 g of water with a high-speed rotating agitator in the preparation step of the reassembled body of the fine powder.

The properties of the SAPs of Examples 19 to 24 and Comparative Examples 11 to 13 were measured and the results are listed in the following Table 4.

TABLE 4

| | First Polymer | Second Polymer (amount of polymer (g): amount of water (g)) | Properties of final SAP | | | |
|---|---|---|---|---|---|---|
| | | | Content of fine powder (weight %) | Water holding capacity (g/g) | Absorbing power under pressure of 0.7 psi (g/g) | Penetrability (seconds) |
| Example 19 | Preparation Example 1 | Preparation Example 2 (5:100) | 2.1 | 34.6 | 22.8 | 148 |
| Example 20 | Preparation Example 1 | Preparation Example 2 (10:100) | 2.1 | 35.4 | 22.3 | 152 |
| Example 21 | Preparation Example 1 | Preparation Example 2 (20:100) | 2.0 | 36.8 | 20.6 | 187 |
| Example 22 | Preparation Example 3 | Preparation Example 4 (1:50) | 2.6 | 30.9 | 24.6 | 70 |
| Example 23 | Preparation Example 3 | Preparation Example 4 (1:150) | 2.4 | 30.4 | 24.8 | 76 |
| Example 24 | Preparation Example 3 | Preparation Example 4 (1:200) | 2.3 | 30.4 | 25.0 | 68 |
| Comparative Example 11 | Preparation Example 3 | Only water 50 g | 5.1 | 31.8 | 24.0 | 162 |
| Comparative Example 12 | Preparation Example 3 | Only water 150 g | 4.6 | 31.6 | 24.1 | 158 |
| Comparative Example 13 | Preparation Example 3 | Only water 200 g | 3.6 | 31.6 | 24.2 | 160 |

*content of fine powder less than 150 μm (%): result of ball-mill test

Generally, the aggregation strength of the fine powders is high when a large amount of water is used for preparing the reassembled body of the fine powder. However, referring to Table 4, there is not much difference in the aggregation strength according to variation of the amount of water used in the preparation method of the present invention. It seems because not only water but also the hydrogel polymer is used as the second polymer in the reassembling step of the fine powders, and the hydrogel polymer plays a role of binder and water is uniformly distributed between the fine powder particles so that the uniform reassembled body of the fine powder is formed.

What is claimed is:

1. A method of preparing a super absorbent polymer, including the steps of:
preparing a first hydrogel polymer by carrying out a thermal polymerization or photo polymerization of a monomer composition including a water-soluble ethylene-based unsaturated monomer and a polymerization initiator;
preparing a second hydrogel polymer by carrying out a thermal polymerization or photo polymerization of a monomer composition including a water-soluble ethylene-based unsaturated monomer and a polymerization initiator;
drying and milling the first hydrogel polymer and distributing the first hydrogel polymer into a fine powder having a particle diameter below 150 μm and a base resin having a particle diameter of 150 μm to 850 μm;
fabricating a reassembled body of the fine powder by mixing the fine powder and the second hydrogel polymer; and
mixing the reassembled body of the fine powder with the first hydrogel polymer, and drying and milling the reassembled body of the fine powder mixed with the first hydrogel polymer,
wherein the second hydrogel polymer has higher water holding capacity than the first hydrogel polymer.

2. The method according to claim 1, wherein the first hydrogel polymer has the water holding capacity of 30 to 50 g/g and the second hydrogel polymer has the water holding capacity of 35 to 60 g/g.

3. The method according to claim 1, wherein the second polymer has higher water soluble component content than the first polymer.

4. The method according to claim 3, wherein the water soluble component content of the first polymer is 5 to 30 weight % and the water soluble component content of the second polymer is 6 to 35 weight %.

5. The method according to claim 1, wherein the second hydrogel polymer is in a free-swollen state with water.

6. The method according to claim 5, wherein the second hydrogel polymer is free-swollen with water so as to contain about 50 to about 50,000 weight % of water based on the weight of the second polymer.

7. The method according to claim 1, wherein the step of fabricating the reassembled body of the fine powder is carried out by mixing 10 to 200 parts by weight of the second hydrogel polymer with 100 parts by weight of the fine powder.

8. The method according to claim 1, further including a surface crosslinking step after the step of drying and milling the reassembled body of the fine powder and the first hydrogel polymer.

9. A super absorbent polymer, prepared by the method of claim 1.

10. The super absorbent polymer according to claim 9, having the water holding capacity of 20 to 50 g/g when it is measured according to EDANA method WSP 241.2.

11. The super absorbent polymer according to claim 9, having the penetrability of 200 seconds or less.

12. The super absorbent polymer according to claim 9, wherein the content of the fine powder of which the particle diameter is below 150 μm is 5 weight % or less.

* * * * *